(12) United States Patent
McKenzie et al.

(10) Patent No.: US 8,206,717 B2
(45) Date of Patent: Jun. 26, 2012

(54) ANTIBODIES AGAINST IL-25

(75) Inventors: Andrew Neil James McKenzie, Cambridge (GB); Sarah Ballantyne, Cambridge (GB)

(73) Assignee: Medical Research Council, London (GB)

( * ) Notice: Subject to any disclaimer, the term of this patent is extended or adjusted under 35 U.S.C. 154(b) by 171 days.

(21) Appl. No.: 12/596,053

(22) PCT Filed: Apr. 17, 2008

(86) PCT No.: PCT/GB2008/001365
§ 371 (c)(1), (2), (4) Date: Oct. 15, 2009

(87) PCT Pub. No.: WO2008/129263
PCT Pub. Date: Oct. 30, 2008

(65) Prior Publication Data
US 2010/0129380 A1  May 27, 2010

Related U.S. Application Data

(60) Provisional application No. 60/912,474, filed on Apr. 18, 2007.

(30) Foreign Application Priority Data

Apr. 18, 2007 (GB) .................................. 0707505.4

(51) Int. Cl.
A61K 39/00 (2006.01)
A61K 39/395 (2006.01)
C07K 16/00 (2006.01)
C07K 16/22 (2006.01)
C07K 16/24 (2006.01)
C12N 15/00 (2006.01)
C12N 15/13 (2006.01)
C12N 15/63 (2006.01)

(52) U.S. Cl. ............... 424/158.1; 424/133.1; 424/135.1; 424/139.1; 424/141.1; 424/142.1; 424/145.1; 530/387.1; 530/387.3; 530/387.9; 530/388.1; 530/388.15; 530/388.23; 536/23.1; 536/23.53; 435/69.1; 435/320.1; 435/325

(58) Field of Classification Search ........................ None
See application file for complete search history.

(56) References Cited

U.S. PATENT DOCUMENTS

2003/0008815 A1* 1/2003 Chen et al. ...................... 514/12

FOREIGN PATENT DOCUMENTS

| WO | WO 92/01047 A1 | 1/1992 |
| WO | WO 2006/094384 A1 | 9/2006 |
| WO | WO 2007/044450 A2 | 4/2007 |
| WO | WO 2010/038155 A2 | 4/2010 |

OTHER PUBLICATIONS

Paul, Fundamental Immunology, 1993, pp. 292-295.*
Casset et al. (2003, Biochem Biophys Res Comm. 307:198-205).*
MacCallum et al. (1996, J Mol Biol. 262:732-745.*
Vajdos et al. (2002, J Mol Biol. 320:415-428.*
Holm et al. (2007, Mol Immunol. 44:1075-1084).*
Chen et al. (1999, J Mol Biol. 293:865-881).*
Angkasekwinai, P., et al., "Interleukin 25 Promotes the Initiation of Proallergic Type 2 Responses," JEM, 204(7):1509-1517 (Jul. 2007).
Angkasekwinai, P., et al., "The Role of Il-25 in Airway Allergic Response," J Allergy Clin Immunol, 119(1):S134 (Jan. 2007). (From J Allergy Clin Immunol, Jan. 2007, Abstract No. 530).
Ballantyne, S.J., et al., "Blocking Il-25 Prevents Airway Hyper-responsiveness in Allergic Asthma," J Allergy Clin Immunol, 120(6):1324-1331 (Dec. 2007).
Budelsky, A.L., et al., "Transgenic Mice Overexpressing Human IL-17E Exhibit an Asthma-Like Phenotype that is Exacerbated in an Ovalbumin-Induced Model of Asthma," J Allergy Clin Immunol, 117(2):S253 (Feb. 2006). (From J Allergy Clin Immunol, Feb. 2006, Abstract No. 980).
Davies, J. and Riechmann, L , "Affinity Improvement of Single Antibody VH Domains: Residues in All Three Hypervariable Regions Affect Antigen Binding," Immunotechnology, 2(3):169-179 (Sep. 1996).
Fallon, P.G., et al., "Identification of an Interleukin (IL)-25-Dependent Cell Population that Provides IL-4, IL-5, and IL-13 at the Onset of Helminth Expulsion," JEM, 203(4):1105-1116 (Apr. 2006).
Fort, M.M., et al., "IL-25 Induces IL-4, IL-5, and IL-13 and Th2-Associated Pathologies In Vivo," Immunity, 15(6):985-995 (Dec. 2001).
Holt, L.J., et al., "Domain Antibodies: Proteins for Therapy," Trends in Biotechnology, 21(11):484-490 (Nov. 2003).
Kawaguchi, M., et al., "IL-17 Cytokine Family," J Allergy Clin Immunol, 114(6):1265-1273 (Dec. 2004).
Létuvé, S., et al., "IL-17E Upregulates the Expression of Proinflammatory Cytokines in Lung Fibroblasts," J Allergy Clin Immunol, 117(3):590-596 (Mar. 2006).
Little, M., et al., "Of Mice and Men: Hybridoma and Recombinant Antibodies," Immunology Today, 21(8):364-370 (Aug. 2000).
Marks, J.D., et al., "By-Passing Immunization. Human Antibodies from V-Gene Libraries Displayed on Phage," Mol Biol, 222(3):581-597 (Dec. 1991).
Owyang, a.M., et al., "Interleukin 25 Regulates Type 2 Cytokine-Dependent Immunity and Limits Chronic Inflammation in the Gastrointestinal Tract," JEM, 203(4):843-849 (Apr. 2006). R&D Systems, "Monoclonal Anti-Human IL-17E Antibody," [online], Mar. 2007 [retrieved on Jul. 24, 2007]. Retrieved from the Internet URL: http://www.rndsystems.com/pdf/mab1258.pdf.
Sharkhuu, T., et al., "Mechanism of Interleukin-25 (IL-17E)-Induced Pulmonary Inflammation and Airways Hyper-Reactivity," Clinical and Experimental Allergy, 36(12):1575 — 1583 (Dec. 2006).
Tamachi, T., et al., "IL-25 Enhances Allergic Airway Inflammation by Amplifying a $T_H2$ Cell-Dependent Pathway in Mice," J Allergy Clin Immunol, 118(3):606-614 (Sep. 2006).
Patents Act 1977: Search Report under Section 17 (1 page) issued in United Kingdom Application No. GB0707505.4, Jul. 27, 2007.

(Continued)

Primary Examiner — Elizabeth C Kemmerer
(74) Attorney, Agent, or Firm — Hamilton, Brook, Smith & Reynolds, P.C.

(57) ABSTRACT

The invention provides the antibody 2C3 and target binding members based on 2C3 which binds interleukin-25. These are useful in therapy, e.g. the treatment of asthma.

18 Claims, 3 Drawing Sheets

OTHER PUBLICATIONS

International Search Report (6 pages) issued in International Application No. PCT/GB2008/001365, Aug. 14, 2008.
International Preliminary Report on Patentability (8 pages) issued in International Application No. PCT/GB2008/001365, Oct. 20, 2009.
Office Action from European Patent Office for EP 08 737 025.0, dated Jan. 19, 2010.
International Search Report (17 pages) issued in International Application No. PCT/IB2009/007302, Apr. 8, 2010.
Almagro, J.C. and Fransson, J., "Humanization of Antibodies," *Frontiers in Bioscience*, 13:1619-1633 (Jan. 2008).
Dall'Acqua, W.F., et al., "Antibody Humanization by Framework Shuffling," *Methods*, 36:43-60 (2005).
Lazar, G.A., et al., "A Molecular Immunology Approach to Antibody Humanization and Functional Optimization," *Molecular Immunology*, 44:1986-1998 (2007).

* cited by examiner

SEQUENCE LISTING

```
<160> NUMBER OF SEQ ID NOS: 16

<210> SEQ ID NO 1
<211> LENGTH: 363
<212> TYPE: DNA
<213> ORGANISM: Mus musculus

<400> SEQUENCE: 1
gaggtccagc tgcaacagtc tggacctgag ctggtgaagc ctggagcttc aatgaagata      60
tcctgcaagg cttctggtta ctccttcact gactacacca tgaactgggt gaagcagagc     120
catggaaaga accttgagtg gattggactt attaatcctt acaatggtgg tactagctac     180
aaccagaact tcaagggcaa ggccacatta actgtagaca agtcatccag cacagcctac     240
atggagctcc tcagtctgac atctgaggac tctgcagtct attactgtgc aagagagggc     300
tatgatggtt acctttactt tgctatggac tactggggtc aaggaacctc agtcaccgtc     360
tcc                                                                    363

<210> SEQ ID NO 2
<211> LENGTH: 121
<212> TYPE: PRT
```

<213> ORGANISM: Mus musculus

<400> SEQUENCE: 2

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Asn Phe
50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Glu Gly Tyr Asp Gly Tyr Leu Tyr Phe Ala Met Asp Tyr Trp
            100                 105                 110

Gly Gln Gly Thr Ser Val Thr Val Ser
            115                 120

<210> SEQ ID NO 3
<211> LENGTH: 321
<212> TYPE: DNA
<213> ORGANISM: Mus musculus

<400> SEQUENCE: 3
gatatccaga tgacacagac tacatcctcc ctgtctgcct ctctgggaga cagagtcacc      60
atcagttgca gtgcaagtca gggcattagc aattatttaa actggtatca gcagaaagca     120
gatggaactg ttgaactcct gatctattac acatcaagtt tacactcagg agtcccatca     180
aggttcagtg gcagtgggtc tgggacagat tattctctca ccatcagcaa cctggaacct     240
gaagatattg ccacttacta ttgtcagcag tatagtaagc ttccgtacac gttcggaggg     300
gggaccaagc tggaaataaa a                                               321

<210> SEQ ID NO 4
<211> LENGTH: 107
<212> TYPE: PRT
<213> ORGANISM: Mus musculus

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Ala Asp Gly Thr Val Glu Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105

<210> SEQ ID NO 5
<211> LENGTH: 5

```
<212> TYPE: PRT
<213> ORGANISM: Mus musculus

<400> SEQUENCE: 5

Asp Tyr Thr Met Asn
1               5

<210> SEQ ID NO 6
<211> LENGTH: 17
<212> TYPE: PRT
<213> ORGANISM: Mus musculus

<400> SEQUENCE: 6

Leu Ile Asn Pro Tyr Asn Gly Gly Thr Ser Tyr Asn Gln Asn Phe Lys
1               5                   10                  15

Gly

<210> SEQ ID NO 7
<211> LENGTH: 13
<212> TYPE: PRT
<213> ORGANISM: Mus musculus

<400> SEQUENCE: 7

Glu Gly Tyr Asp Gly Tyr Leu Tyr Phe Ala Met Asp Tyr
1               5                   10

<210> SEQ ID NO 8
<211> LENGTH: 15
<212> TYPE: PRT
<213> ORGANISM: Mus musculus

<400> SEQUENCE: 8

Ser Ala Ser Gln Gly Ile Ser Asn Tyr Leu Asn Trp Tyr Gln Gln
1               5                   10                  15

<210> SEQ ID NO 9
<211> LENGTH: 7
<212> TYPE: PRT
<213> ORGANISM: Mus musculus

<400> SEQUENCE: 9

Tyr Thr Ser Ser Leu His Ser
1               5

<210> SEQ ID NO 10
<211> LENGTH: 9
<212> TYPE: PRT
<213> ORGANISM: Mus musculus

<400> SEQUENCE: 10

Gln Gln Tyr Ser Lys Leu Pro Tyr Thr
1               5

<210> SEQ ID NO 11
<211> LENGTH: 26
<212> TYPE: DNA
<213> ORGANISM: Artificial Sequence
<220> FEATURE:
<223> OTHER INFORMATION: Synthetic sequence: VH 5prime Primer

<400> SEQUENCE: 11
atggratgga gckggrtctt tmtctt                                          26

<210> SEQ ID NO 12
<211> LENGTH: 21
```

```
<212> TYPE: DNA
<213> ORGANISM: Artificial Sequence
<220> FEATURE:
<223> OTHER INFORMATION: Synthetic sequence: Heavy chain constant region
      primer

<400> SEQUENCE: 12
cagtggatag acagatgggg g                                               21

<210> SEQ ID NO 13
<211> LENGTH: 25
<212> TYPE: DNA
<213> ORGANISM: Artificial Sequence
<220> FEATURE:
<223> OTHER INFORMATION: Synthetic sequence: Vkappa 5prime primer

<400> SEQUENCE: 13
atggtrtccw casctcagtt ccttg                                           25

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence: Light chain constant region
      primer

<400> SEQUENCE: 14
actggatggt gggaagatgg                                                 20

<210> SEQ ID NO 15
<211> LENGTH: 420
<212> TYPE: DNA
<213> ORGANISM: Mus musculus

<400> SEQUENCE: 15
atggratgga gckggrtctt tmtcttcctc ctgtcgggaa ctgcaggtgt ccactctgag      60
gtccagctgc aacagtctgg acctgagctg gtgaagcctg gagcttcaat gaagatatcc    120
tgcaaggctt ctggttactc cttcactgac tacaccatga actgggtgaa gcagagccat    180
ggaaagaacc ttgagtggat tggacttatt aatccttaca atggtggtac tagctacaac    240
cagaacttca agggcaaggc cacattaact gtagacaagt catccagcac agcctacatg    300
gagctcctca gtctgacatc tgaggactct gcagtctatt actgtgcaag agagggctat    360
gatggttacc tttactttgc tatggactac tggggtcaag aacctcagt caccgtctcc    420

<210> SEQ ID NO 16
<211> LENGTH: 381
<212> TYPE: DNA
<213> ORGANISM: Mus musculus

<400> SEQUENCE: 16
atggtrtccw casctcagtt ccttggtctc ctgttgctct gttttcaagg taccagatgt      60
gatatccaga tgacacagac tacatcctcc ctgtctgcct ctctgggaga cagagtcacc    120
atcagttgca gtgcaagtca ggcattagc aattatttaa actggtatca gcagaaagca    180
gatggaactg ttaactcct gatctattac acatcaagtt tacactcagg agtcccatca    240
aggttcagtg gcagtgggtc tgggacagat tattctctca ccatcagcaa cctggaacct    300
gaagatattg ccacttacta ttgtcagcag tatagtaagc ttccgtacac gttcggaggg    360
gggaccaagc tggaaataaa a                                               381
```

ANTIBODIES AGAINST IL-25

RELATED APPLICATIONS

This application is the U.S. National Stage of International Application No. PCT/GB2008/001365, filed on Apr. 17, 2008, published in English, which claims the benefit of U.S. Provisional Application No. 60/912,474, filed on Apr. 18, 2007. This application claims priority under 35 U.S.C.§119 or 365 to Great Britain Application No. 0707505.4, filed Apr. 18, 2007. The entire teachings of the above applications are incorporated herein by reference.

FIELD OF THE INVENTION

The present invention relates to antibodies, including binding fragments thereof, directed to interleukin 25 (IL-25). Preferred embodiments of the present invention employ the antibody VH and/or VL domains of the antibody 2C3. In another aspect the invention provides one or more of the CDRs of the VH and VL domains disclosed herein grafted into a human VH and VL framework regions, respectively.

BACKGROUND OF THE INVENTION

Asthma is a common chronic inflammatory disorder of the airways. The number of sufferers has increased dramatically over recent decades and the World Health Organisation estimates that in the region of 300 million people worldwide suffer from asthma. Allergic asthma is characterised by uncontrollable airways hyperresponsiveness (AHR) induced by a variety of provocative stimuli and is associated with type-2 inflammatory infiltrates into the lungs.

Type-2 cytokines play an important role in mediating protective immunity to parasitic helminth infection, regulating effector functions such as B cell growth and IgE secretion, inducing goblet cell hyperplasia and associated mucus production, eosinophilia, mastocytosis and fibrosis (1). It is the central roles played by these cytokines in the regulation of these effector functions that have made them key therapeutic targets in asthma. Indeed, mouse models in which these cytokines are over-expressed show significant characteristics of asthma. Surprisingly then, efforts to ameliorate experimental asthma by blocking specific type-2 cytokines have, with the exception of inhibiting IL-13, proven unsuccessful.

Inhibition of IL-13 suppresses both AHR and airway inflammation although the mechanism remains unclear (2, 3). However, given the complex pathophysiology and poorly understood etiology of asthma, it is uncertain whether targeting individual pathways will ultimately prove successful therapeutically.

Recently, over-expression of IL-25/IL-17E, a member of the structurally related IL-17 cytokine family (8), has been shown to induce type-2 responses in vivo (4-6) and increase responsiveness to airway agonists (7). Il25$^{-/-}$ mice failed to expel helminth parasites; a key indicator of an ineffectual type-2 response (9, 10).

The basic structure of an antibody is well known in the art. A naturally-occurring antibody usually has four polypeptide chains: two identical heavy chains and two identical light chains connected by disulphide bonds. The heavy and light chains each have a constant region and a variable region (or domain). The variable regions are primarily responsible for antigen binding. Within each variable region, three subregions, known as the complementarity-determining regions (CDRs), make contact with the antigen. The CDRs of each variable domain are numbered, from the N-terminal to the C-terminal, as CDR1, CDR2 and CDR3. Between and N- and C-terminal to the CRDs are four so-called framework regions, which make few if any contacts with the antigen. More details regarding the structures of antibodies are illustrated in many of the documents cited below, which are incorporated herein by reference.

DISCLOSURE OF THE INVENTION

The present inventors have produced antibodies against IL-25 and identified an antibody molecule which binds with high affinity and specificity to IL-25. Since human and mouse IL-25 share 80% sequence identity it was believed that it would be unlikely that it would be possible to generate useful anti-IL-25 antibodies by conventional immunisation of either mice or rats, since the degree of similarity would reduce the number of immunogenic epitopes. Furthermore, the receptor-ligand interface was likely to show the greatest degree of conservation thereby precluding the generation of antibodies capable of blocking the interaction of IL-25 with its receptor. To overcome these problems the present inventors immunised mice that had been engineered to lack IL-25 (IL-25–/–) expression with the belief that this approach would increase the likelihood of developing antibodies directed against the IL-25/IL-25R interface.

This approach was highly successful at generating antibodies against IL-25, probably due to the IL-25 itself enhancing the humoral immune response. However, even using this approach only two blocking antibodies out of the seventy screened were identified, and only one of these could be recovered.

Having overcome the problem of the similarity between murine and human IL-25 which was believed to preclude the generation of effective blocking antibodies through conventional means, it is believed that this sequence similarity may allow the generation of an antibody which is equally effective at blocking mouse and human IL-25 interacting with their receptors. The present invention now shows that this is indeed the case.

Although other antibodies to IL-25 are in existence the present invention is believed to be the first demonstration of such antibodies able to block IL-25 bioactivity. In particular, the present disclosure provides test conducted in murine models of asthma which show that an antibody of the invention has advantageous and unexpected properties, especially its ability to prevent or reduce airway hyperresponsiveness in vivo, a key symptom of asthma.

Although administration of a soluble IL-25R-Fc fusion protein has also been reported to reduce type-2 airways inflammation, the effects were less dramatic than those reported herein and critically AHR was not assessed (11). We now demonstrate that IL-25 plays critical roles in airways inflammation and AHR, acting initially to enhance type-2 cytokine mediated inflammation, but also playing an important role in the induction of AHR independently of the classical type-2 cytokines. The identification of IL-25-dependent AHR offers the possibility of identifying new therapeutic targets that lie downstream of IL-25. At present we do not know whether IL-25 acts directly on airways smooth muscle to induce broncho-constriction or if its effects are mediated through the induction of known bronchoconstrictors such as the leukotrienes. However, the biphasic activity of IL-25 makes it an excellent therapeutic target for the suppression of airway inflammation and the inhibition of airways hyperresponsiveness in vivo.

SUMMARY OF THE INVENTION

Accordingly, the present invention relates to the novel antibody, and more generally target binding members comprising the antibody CDR sequences, as well as the use of target binding members in the treatment of conditions such as asthma.

In one embodiment, the invention provides a target binding member that binds IL-25 and which comprises an antibody VH domain comprising a VH CDR3 with the amino acid sequence of SEQ ID NO. 7. This is the VH CDR3 sequence of the antibody 2C3 of the present invention.

In more specific embodiments, a target binding member of the invention is a VH domain which comprises a VH CDR3 of SEQ ID NO:7 together with a CDR1 of SEQ ID NO:5 and a CDR2 of SEQ ID NO:6.

The VH domain may have human framework regions, or the framework regions shown in SEQ ID NO:2.

The VH domains may be paired with a VL domain of the invention, e.g. a VL domain with a CDR1 of SEQ ID NO:8, a CDR2 of SEQ ID NO:9 and a CDR3 of SEQ ID NO:10. These CDRs may be in a VL domain having human framework regions or may be the VL domain of SEQ ID NO:4.

Thus in one aspect, the present invention provides a target binding member which binds IL-25 and which comprises the 2C3 VH domain (SEQ ID NO:2) and/or the 2C3 VL domain (SEQ ID NO:4).

The invention also provides isolated nucleic acid encoding the target binding members of the invention, vectors comprising the nucleic acid and methods of expressing the nucleic acid in a host cell to produce target binding members of the invention.

The invention further provides the use of target binding members of the invention, for example in the form of a pharmaceutical composition, for the treatment of diseases, including asthma.

These and further aspects of the invention are described in further detail below and with reference to the accompanying examples. Zone Name: B3,AMD

SEQUENCES

Figure 1:
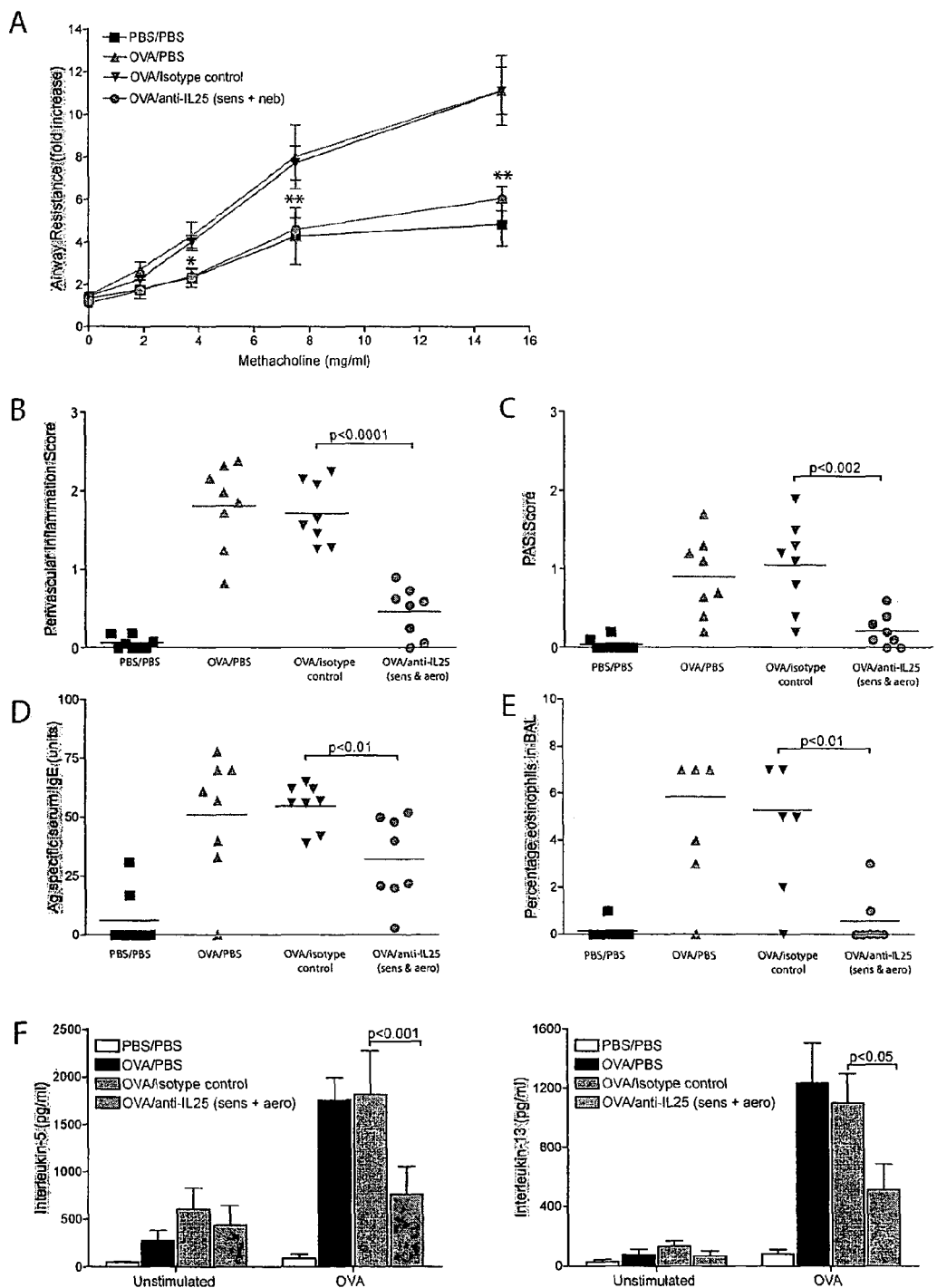
FIG. 1 shows neutralisation of IL-25 before sensitisation and also during asthma challenge. (A) Methacholine sensitivity of OVA-sensitised mice was determined one day after the last aerosolised antigen challenge. Data are combined from 2 experiments and represent the mean±SEM of 14-18 mice/group. (*$p<0.05$ versus isotype control, **$p<0.01$ versus isotype control) (B) Lung sections were stained with giemsa and scored for perivascular infiltration, n=8 per group. (C) Mucus content was determined by periodic acid Schiff (PAS) staining of lung sections, n=8 per group. (D) Antigen-specific serum IgE was measured by ELISA, OD reading were converted to arbitrary units by comparison with a standard serum n=8 per group. (E) The proportion of eosinophils in BAL was determined by differential cell counting of cytospins stained with giemsa, n=6 per group. (F) Antigen-induced cytokine production from restimulated mediastinal lymph node cells. Protein levels were determined by ELISA, n=6 per group. Symbols represent individual animals and the mean is represented by a bar. Data are representative of at least 2 independent experiments. Sens=antibody administered prior to sensitization, aero=antibody administered 4 hours prior to each aerosol challenge.

The target binding members of the present invention are described further herein with reference to the following sequence identification numbers:
SEQ ID NO. 1 2C3 VH encoding nucleotide sequence
SEQ ID NO. 2 2C3 VH amino acid sequence
SEQ ID NO. 3 2C3 VL encoding nucleotide sequence
SEQ ID NO. 4 2C3 VL amino acid sequence
SEQ ID NO. 5 2C3 VH CDR1 amino acid sequence
SEQ ID NO. 6 2C3 VH CDR2 amino acid sequence
SEQ ID NO. 7 2C3 VH CDR3 amino acid sequence
SEQ ID NO. 8 2C3 VL CDR1 amino acid sequence
SEQ ID NO. 9 2C3 VL CDR2 amino acid sequence
SEQ ID NO. 10 2C3 VL CDR3 amino acid sequence Further sequences are set out in the accompanying sequence listing.

DETAILED DESCRIPTION OF THE INVENTION

Target Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate.

This application is concerned with antigen-antibody type reactions. Accordingly, a target binding member of the invention will comprise at least a portion of an antibody molecule, more particularly at least part of the antigen-binding domain of such a molecule.

In general, the heavy chain variable region (VH domain) of an antibody plays a significant role in the binding of an antibody to an antigen. The CDR3 region of a VH domain has been found to be more diverse than the CDR1 and CDR2 regions, and thus in most antibodies provides specificity for the target of the antibody. Thus target binding members of the invention are thus based around the VH CDR3 region of the 2C3 antibody. Target binding members of the invention more preferably comprise all three CDRs of the VH regions of the 2C3 antibody.

The structure of a target binding member which comprises a CDR of the invention will generally be of a heavy or light chain sequence of an antibody molecule or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof. A number of academic and commercial on-line resources are available to query this database. For example, see Martin, A. C. R. Accessing the Kabat Antibody Sequence Database by Computer PROTEINS: *Structure, Function and Genetics*, 25 (1996), 130-133 and the associated on-line resource.

Generally, a target binding member comprises a VH domain paired with a VL domain to provide an antibody antigen binding domain, although as discussed further below a VH domain alone may be used to bind antigen. In one preferred embodiment, the 2C3 VH domain (SEQ ID NO. 2) is paired with the 2C3 VL domain (SEQ ID NO. 4), so that an antibody antigen binding site is formed comprising both the 2C3 VH and VL domains. In other embodiments, the 2C3 VH is paired with a VL domain other than the 2C3 VL.

Light-chain promiscuity is well established in the art, as discussed further herein.

A target binding member according to the present invention may bind IL-25 with an affinity substantially similar to that of 2C3, e.g. ±10%. A target binding member will generally be specific for IL-25. Thus the target binding member will not show any significant binding to molecules other than its specific binding partner(s). For example, it has been found that the 2C3 antibody does not cross-react with IL-4, IL-5 and IL-13 and thus avoidance of such cross-reactivity to other cytokines implicated in asthma and similar processes is a desirable feature of target binding members of the invention.

Typically, specificity may be determined by means of a binding assay such as ELISA employing a panel of antigens. A target binding member according to the present invention may recognise IL-25 and not other members of the IL-17 family, particular any one of IL-17A, IL-17B and IL-17C; more preferably all three of IL-17A, IL-17B and IL-17C. Binding of a target binding member according to the invention with IL-25 may be abolished by competition with recombinant IL-25.

Binding affinity and neutralisation potency of different target binding members can be compared under appropriate conditions.

Antibody Molecule

This describes an immunoglobulin whether natural or partly or wholly synthetically produced. It has been shown that fragments of a whole antibody can perform the function of binding antigens. Thus reference to an antibody also covers any polypeptide or protein comprising an antibody binding fragment.

Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against IL-25, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996). It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400.

Preferably the CDR regions are grafted into a human framework region. The human framework region may be selected by a number of methods, e.g. by comparing the mouse framework region or mouse V region sequences with known human framework or V region sequences and selecting a human framework region which has the highest, or one of the highest degrees of amino acid similarity or identity. Modifications to framework regions of native human sequences may be made in order to further optimize the resulting CDR-grafted antibodies.

Although in a preferred aspect of the invention antibody molecules comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single chain binding domains, these domains may be used to screen for complementary domains capable of forming a two-domain target binding member able to bind IL-25, as discussed further herein below.

Antibody molecules of the present invention may further comprise antibody constant regions or parts thereof. For example, a VL domain may be attached at its C-terminal end to antibody light chain constant domains including human Cκ or Cλ chains, preferably Cλ chains. Similarly, a target binding member based on a VH domain may be attached at its C-terminal end to all or part of an immunoglobulin heavy chain derived from any antibody isotype, e.g. IgG, IgA, IgE and IgM and any of the isotype sub-classes, particularly IgG1 and IgG4. IgG4 is preferred. Fc regions such as Δnab and Δnac as disclosed in WO99/58572 may be employed.

Chimeric molecules comprising an target binding domain, or equivalent, fused to another polypeptide are therefore included. Cloning and expression of chimeric antibodies are described in EP-A-0120694 and EP-A-0125023.

Framework regions of antibody molecules of the invention may also include glycosylation sequences that include one or more glycosylation sites. Depending upon the host cell in which the target binding member is expressed, the pattern of glycosylation may vary. Thus nucleic acid constructs that encode glycosylation sites may be modified to remove the site or alternatively such sites may be introduced into the protein. For example, N-glycosylation sites in eukaryotic proteins are characterized by an amino acid triplet Asn-X-Y, wherein X is any amino acid except Pro and Y is Ser or Thr. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

Antigen-Binding Domain

This describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises at least a substantial portion of an antibody light chain variable region (VL) and at least a substantial portion of an antibody heavy chain variable region (VH).

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of target binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Comprise

This is generally used in the sense of include, that is to say permitting the presence of one or more features or components.

Isolated

This refers to the state in which target binding members of the invention, or nucleic acid encoding such binding members, will generally be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo.

Target binding members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Target binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Additional Features of Target Binding Members.

In addition to antibody sequences, a target binding member according to the present invention may comprise other amino acids, e.g. forming a peptide or polypeptide, such as a folded domain, or to impart to the molecule another functional characteristic in addition to ability to bind antigen. Target binding members of the invention may carry a detectable label, or may be conjugated to a toxin or enzyme (e.g. via a peptidyl bond or linker).

Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Where the additional feature is a polypeptide domain or label, the target binding member may be produced by recombinant techniques, i.e. by the expression of nucleic acid encoding a fusion of the target binding member and the further domain.

Further Target Binding Members of the Invention

Sequence Variants

Variants of the VH and VL domains and CDRs of which the sequences are set out herein and which can be employed in target binding members for IL-25 can be obtained by means of methods of sequence alteration or mutation and screening. Such methods are also provided by the present invention.

A target binding member according to the invention may also be one which competes for binding to antigen with any target binding member which both binds the antigen and comprises a target binding member, VH and/or VL domain disclosed herein, or VH CDR3, of 2C3, or a variant of any of these whose sequence is substantially as set out herein. Thus, a further aspect of the present invention provides a target binding member comprising a human antibody antigen-binding site which competes with 2C3 for binding to IL-25. Competition between binding members may be assayed easily in vitro, for example using ELISA and/or by tagging a specific reporter molecule to one binding member which can be detected in the presence of other untagged binding member(s), to enable identification of target binding members which bind the same epitope or an overlapping epitope.

Various methods are available in the art for obtaining target binding members against IL-25 and which may compete with 2C3 for binding to IL-25.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

In one aspect, a CDR amino acid sequence substantially as set out herein is carried as a CDR in a human variable domain or a substantial portion thereof. The VH CDR3 sequences substantially as set out herein represent preferred embodiments of the present invention and it is preferred that each of these is carried as a VH CDR3 in a human heavy chain variable domain or a substantial portion thereof.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

Sequence variants of target binding members of the invention may be generated by carrying out random mutagenesis of one or both of the 2C3 VH and/or VL genes to generate mutations within the entire variable domain. Such a technique is described by Gram et al (1992, Proc. Natl. Acad. Sci., USA, 89:3576-3580), who used error-prone PCR.

Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

All the above described techniques are known as such in the art and in themselves do not form part of the present invention. The skilled person will be able to use such techniques to provide target binding members of the invention using routine methodology in the art.

Accordingly, in a further aspect the invention provides a method for obtaining an antibody against IL-25 which comprises:
  providing a starting nucleic acid encoding a target binding member that has one or more of the CDR sequences of SEQ ID NO:2 or SEQ ID NO:4;
  modifying said nucleic acid to alter the CDR sequence or sequences;
  expressing said modified target binding member; and
  testing said modified target binding member for binding against IL-25.

Preferably the modification will be performed on a plurality of starting nucleic acid molecules to provide a repertoire of modified sequences having a diversity of binding affinities.

In one aspect, the starting nucleic acid comprises all three heavy chain CDRs of SEQ ID NO:2, either in the form of SEQ ID NO:2 itself or carried in another framework sequence.

In one embodiment, the modifications may be directed at a single CDR, e.g. the CDR3, or the modifications may be directed to two or three CDR regions simultaneously.

Production of CDR3-Based Target Binding Members

Variable domains employed in the invention may be obtained from any germ-line or rearranged human variable domain, or may be a synthetic variable domain based on consensus sequences of known human variable domains. A CDR sequence of the invention (e.g. CDR3) may be introduced into a repertoire of variable domains lacking a CDR (particularly CDR3), using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide target binding members of the invention. The repertoire may then be displayed in a suitable host system such as the phage display system of WO92/01047 so that suitable target binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (Nature, 1994, 370:389-391), who describes the technique in relation to a β-lactamase gene but observes that the approach may be used for the generation of antibodies.

A further aspect of the invention thus provides a method of preparing a target binding member specific for IL-25, which method comprises:
  (a) providing a starting repertoire of nucleic acids encoding a VH domain which either include a CDR3 to be replaced or lack a CDR3 encoding region;
  (b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
  (c) expressing the nucleic acids of said product repertoire;
  (d) selecting a target binding member specific for a IL-25; and
  (e) recovering said target binding member or nucleic acid encoding it.

The product repertoire may be co-expressed, from the same vector or different vector, with a VL domain. The VL domain may be the VL domain of the present invention or may be one or more different VL domains, as described below in relation to chain shuffling.

An analogous method may be employed in which a VL CDR3 of the invention is combined with a repertoire of nucleic acids encoding a VL domain which either include a CDR3 to be replaced or lack a CDR3 encoding region. As with the method above, the VL product repertoire may be co-expressed, from the same vector or different vector, with a VH domain. The VH domain may be the VH domain of the present invention or may be one or more different VH domains, as described below in relation to chain shuffling.

Similarly, one or more, or all three CDRs may be grafted into a repertoire of VH or VL domains which are then screened for a target binding member or target binding members specific for IL-25.

Target binding members obtained in this manner form a further aspect of the invention.

Chain Shuffling

A further aspect of the invention provides a method for obtaining an antibody antigen-binding domain for IL-25, the method comprising providing combining a VH domain of a target binding member of the invention (including variants as discussed above) with one or more VL domains, and testing the VH/VL combination or combinations for antibody-antigen binding domain for IL-25.

Said VL domain may have an amino acid sequence which is substantially as set out herein.

An analogous method may be employed in which one or more sequence variants of a VL domain disclosed herein are combined with one or more VH domains.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain target binding member is selected in accordance with phage display techniques such as those described in that reference.

Thus the present invention provides a method for selection of an antibody molecule for IL-25, the method comprising:
(a) providing a VH domain comprising a target binding member that binds IL-25 and which comprises an antibody VH domain comprising a VH CDR3 with the amino acid sequence of SEQ ID NO. 7;
(b) combining said VH domain with a plurality of antibody VL domains to provide antibody molecules;
(c) screening said antibody molecules for binding to IL-25; and
(d) selecting an antibody molecule which binds IL-25.

The VH and VL domains may be provided in the form of proteins expressed by recombinant DNA, particularly by a phage or phagemid DNA.

The plurality of VL domains may be anything from $10^4$ individual domains upwards, for example from $10^6$ to $10^8$ or $10^{10}$ domains.

Antibody molecules, and nucleic acid encoding such molecules, may form a further part of the present invention.

IL-25

Il-25, also referred to in the art as IL-17E, is available from commercial sources (e.g. R&D Systems, MN, USA) or may be cloned or synthesised by reference to the sequences of IL-25 available in the art. Murine IL-25 (NCBI Protein NP_542767) is described by Hurst et al, 2002 (Ref. 7 below). Human IL-25 (NCBI Protein Q9H293) is described by Fort et al (Ref. 4 below). For production of antibodies or use in immunoassays, fragments of recombinant IL-25 may be used, particularly those truncated at the N-terminal. For example, commercially available recombinant human IL-25 (IL-17E) comprises the mature protein sequence of Tyr 33-Gly 177 of Accession No. Q9H293) and commercially available murine IL-25 comprises residues Val 17-Ala 169 of mouse IL-17E (Accession No. NP 542767).

Nucleic Acids and Vectors

In further aspects, the invention provides an isolated nucleic acid which comprises a sequence encoding a target binding member, a VH domain, or VL domain according to the present invention, and methods of preparing a target binding member, a VH domain, or a VL domain of the invention, which comprise expressing said nucleic acid under conditions to bring about production of said target binding member, VH domain, or VL domain, and recovering it.

Another aspect of the present invention provides nucleic acid, generally isolated, encoding a VH CDR or VL CDR sequence disclosed herein, especially a VH CDR selected from SEQ ID NOs: 5, 6 and 7, a VL CDR selected from SEQ ID NOs: 8, 9 and 10, most preferably 2C3 VH CDR3 (SEQ ID NO. 7).

The nucleic acids of the invention may comprise the sequences, or relevant portions thereof (e.g. CDR-encoding regions) of SEQ ID NO:1 or SEQ ID NO:3. However, codon usage may be varied, e.g. to optimize expression of the sequence in a desired host cell.

The present invention further provides an isolated nucleic acid encoding a target binding member of the present invention. Nucleic acid includes DNA and RNA. In a preferred aspect, the present invention provides a nucleic acid which codes for a CDR or VH or VL domain of the invention as defined above.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

The present invention also provides vectors, for example in the form of plasmids, viruses, e.g. 'phage, or phagemid, cosmids, transcription or expression cassettes which comprise at least one nucleic acid as above.

Suitable vectors can be chosen or constructed, containing appropriate regulatory sequences, including promoter sequences, terminator sequences, polyadenylation sequences, enhancer sequences, marker genes and other sequences as appropriate. For further details see, for example, Molecular Cloning: a Laboratory Manual: 2nd edition, Sambrook et al., 1989, Cold Spring Harbor Laboratory Press.

Vectors of the invention also include viral vectors capable of infecting human cells in vivo, e.g. adenoviral, retroviral or adeno-associated virus vectors. Such vectors may be useful for expression of a target binding member of the invention in the cells of a human or animal subject, to provide for production and delivery of the target binding member to said subject.

A nucleic acid sequence encoding a target binding member of the invention will in one aspect be operably linked to a promoter to effect expression of the target binding member in a host cell. The sequence may include at its 5' end a leader sequence to facilitate expression and/or secretion of the target binding member in and/or from a host cell. Numerous suitable leader sequences are known as such in the art and may be selected by a person of ordinary skill in the art taking account of the host cell.

Many, known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992. The disclosures of Sambrook et al. and Ausubel et al. are incorporated herein by reference.

Host Cells and Production of Target Binding Members

A further aspect provides a host cell transformed with a nucleic acid (e.g. a nucleic acid sequence in the form of a vector) of the invention.

In one embodiment, the nucleic acid of the invention is integrated into the genome (e.g. chromosome) of the host cell. Integration may be promoted by inclusion of sequences which promote recombination with the genome, in accordance with standard techniques.

A yet further aspect provides a method of production of an target binding member of the invention, the method including causing expression from encoding nucleic acid. Such a method may comprise culturing host cells under conditions for production of said target binding member.

Following production by expression a VH or VL domain, or target binding member may be isolated and/or purified using any suitable technique, then used as appropriate. A method of production may comprise a step of isolation and/or purification of the product.

Following purification of the product the target binding member may be modified by physical or chemical means, for example to introduce protective groups that alter, e.g. increase, the stability or biological half-life of the protein. For example, PEGylation of proteins to achieve such effects is known as such in the art and target binding members of the invention may be in PEGylated form.

A method of production may comprise formulating the product into a composition including at least one additional component, such as a pharmaceutically acceptable excipient.

The present invention also provides a recombinant host cell which comprises one or nucleic acids or vectors as above. A nucleic acid encoding any CDR, VH or VL domain, or target binding member as provided itself forms an aspect of the present invention, as does a method of production of the encoded product, which method comprises expression from encoding nucleic acid therefor.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a target binding member, see for recent reviews, for example Ref, M. E. (1993) Curr. Opinion Biotech. 4: 573-576; Trill J. J. et al. (1995) Curr. Opinion Biotech 6: 553-560.

Compositions

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Therapeutic formulations of the target binding member may be prepared for storage by mixing the target binding member having the desired degree of purity with optional physiologically acceptable carriers, excipients, or stabilizers (see e.g. "Remington: The Science and Practice of Pharmacy", 20th Edition, 2000, pub. Lippincott, Williams & Wilkins.), in the form of lyophilized powder or aqueous solutions. Acceptable carriers, excipients or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

For the target binding member to be used for in vivo administration it must be sterile. This is readily accomplished by filtration through sterile filtration membranes, prior to or following lyophilization and reconstitution. The target binding member ordinarily will be stored in lyophilized form or in solution.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Therapeutic Uses of the Invention

The present invention provides for the first time a demonstration that antibodies against IL-25 are effective in preventing or reducing airway hyperresponsiveness in vivo, a key symptom of asthma. Thus in one aspect the invention provides a method of preventing or reducing airway hyperresponsiveness in a subject (e.g. a human) in need of treatment which comprises administering to the subject a target binding member, particularly an antibody molecule, that binds IL-25. In another aspect the invention provides a method of preventing, reducing or treating asthma in a subject in need of treatment which comprises administering to the subject a target binding member, particularly an antibody molecule, that binds IL-25.

The above methods may be practiced with target binding members (including compositions thereof) according to the present invention, which are useful in binding to and preferably antagonising action of IL-25, with therapeutic potential in various diseases and disorders in which IL-25 plays a role. The methods may also be practiced with other target binding members (including compositions thereof) which bind IL-25 that may be obtained as described below in the accompanying examples.

Target binding members (including compositions thereof) according to the invention may be used in a method of treatment (including prophylactic treatment) or diagnosis in human or animal subject. Such a method of treatment or diagnosis (which may include prophylactic treatment) may comprise administering to said subject an effective amount of a target binding member of the invention. Exemplary diseases and disorders are discussed further below.

Also provided is the use of a target binding member (including a compositions thereof) of the invention in the manufacture of a medicament for administration, to a human or animal subject.

Clinical indications in which an anti-IL-25 target binding member may be used to provide therapeutic benefit include any condition in which IL-25 has pathological consequences. Thus in general, the target binding member of the invention may be used in the treatment of any condition associated with an unwanted Th-2 response. For example, the a target binding member of the invention may be used for the treatment of allergy and asthma, particularly asthma.

Anti-IL-25 treatment may be given by injection (e.g. intravenously) or by local delivery methods. Anti-IL-25 may be delivered by gene-mediated technologies. Alternative formulation strategies may provide preparations suitable for oral or suppository route. The route of administration may be determined by the physicochemical characteristics of the treatment, by special considerations for the disease, to optimise efficacy or to minimise side-effects.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered as a bolus intravenously. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

An antibody molecule in some preferred embodiments of the invention is a monomeric fragment, such as F(ab) or scFv. Such antibody fragments may have the advantage of a relatively short half life and less risk of platelet activation, which may be caused by receptor clustering. Clustering which gives rise to platelet activation could be either of IL-25 molecules or of IL-25 with FcγRII molecules, for instance.

If a whole antibody, is used, it is preferably in a form that is unable to activate and/or destroy platelets. The IgG4 isotype or alternatively "designer" isotypes derived from the IgG1 backbone (novel Fc gene constructs WO99/58572, Clark, Armour, Williamson) are preferred choices. Smaller antibody fragments may be used, such as F(ab')$_2$. In addition, whole antibodies or fragments (e.g. F(ab')$_2$ or diabodies) with dual epitope specificity (e.g. for the epitopes recognised by scFv 2C3) may be used. Although such an embodiment may promote receptor clustering, a high association rate to individual receptors may rule out this problem.

Target binding members of the present invention will usually be administered in the form of a pharmaceutical composition, which may comprise at least one component in addition to the target binding member.

A target binding member of the invention may be administered alone or in combination with other treatments, either simultaneously or sequentially dependent upon the condition to be treated. Other treatments may include the administration of suitable doses of pain relief drugs such as non-steroidal anti-inflammatory drugs (e.g. asprin, paracetamol, ibuprofen or ketoprofen) or opiates such as morphine; the administration of anti-emetics; or the administration of at least one other compound active against asthma, generally a bronchodilating agent which produces airway relaxation or enhances mucus clearance, e.g. a beta-agonist (e.g. salbutamol, salmeterol), disodium cromoglycate, steroids or an inhibitor of $PDE_{IV}$.

Assay Methods

The present invention provides a method comprising causing or allowing binding of a target binding member as provided herein to IL-25. As noted, such binding may take place in vivo, e.g. following administration of a target binding member, or nucleic acid encoding a target binding member, or it may take place in vitro, for example in ELISA, Western blotting, immuno-cytochemistry, immuno-precipitation or affinity chromatography.

The amount of binding of target binding member to IL-25 may be determined. Quantitation may be related to the amount of the antigen in a test sample, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a target binding member as above for measuring antigen levels in a competition assay, that is to say a method of measuring the level of antigen in a sample by employing a target binding member as provided by the present invention in a competition assay. This may be where the physical separation of bound from unbound antigen is not required. Linking a reporter molecule to the target binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a target binding member according to the invention for example in a biosensor system.

The mode of determining binding is not a feature of the present invention and those skilled in the art are able to choose a suitable mode according to their preference and general knowledge.

The present invention further extends to a target binding member which competes for binding to IL-25 with any target binding member which both binds the antigen and comprises a V domain including a CDR with amino acid substantially as set out herein or a V domain with amino acid sequence substantially as set out herein. Competition between binding members may be assayed easily in vitro, for example by tagging a specific reporter molecule to one binding member which can be detected in the presence of other untagged binding member(s), to enable identification of target binding members which bind the same epitope or an overlapping epitope. Competition may be determined for example using ELISA or flow cytometry.

A competition reaction may be used to select one or more target binding members such as derivatives of 2C3, which may have one or more additional or improved properties. This is analogous to the selection method for 2C3 in accordance with the invention, except that IL-25 is not eluted from its mini-ligand but from an antibody molecule. This may be important as it should yield a greater proportion of daughter antibodies which directly compete with the parent. Indeed such daughter antibodies as are selected may have a greater affinity for the antigen than the parent (allowing for enhancements in avidity which may result from the display of more than one antibody molecule per phage). Current methods of selecting for "daughter" phage antibodies of improved affinity include:

using concentrations of (labelled) target antigen lower than the dissociation constant of the original parent antibody;

using excess unlabelled target antigen as a competitor as demonstrated in Hawkins et al (1992). However, they do not necessarily specify that the "improved" antibody must displace/occupy the same epitope as the parent. Incorporating the elution step should yield a higher proportion of daughter antibodies which do displace the parent. Daughter antibodies selected in this way may bind a very similar epitope to the parent antibody, but with a greater affinity.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence. Target binding members according to the present invention may be such that their binding for antigen is inhibited by a peptide with or including the sequence given. In testing for this, a peptide with either sequence plus one or more amino acids may be used.

Target binding members which bind a specific peptide may be isolated for example from a phage display library by panning with the peptide(s).

EXAMPLES

Aspects and embodiments of the present invention will now be illustrated by way of example with reference to the following experimentation.

Example 1

Generation of Antibodies Against IL-25

A large panel of antibodies, generated in il25$^{-/-}$ mice immunised against murine IL-25 (R&D Systems), was screened. One of these anti-IL-25 antibodies (2C3) was found to inhibit both the interaction between rmIL-25 and a soluble mIL-25R-Fc fusion protein dose dependently and IL-25-dependent production of IL-13 by primary mouse non-B, non-T cells in an in vitro bioassay. The antibody also inhibited the interaction between hIL-25 and a soluble hIL-25R-Fc fusion. The combination of these properties was investigated further in in vivo systems to demonstrate usefulness in the treatment of asthma.

Example 2

Experimental Model of Allergic Asthma

BALB/c mice were first sensitized with the antigen ovalbumin (OVA), before being challenged with aerosolised OVA. Sensitised and challenged BALB/c mice developed a distinctive asthma phenotype. This was characterised by increased AHR following exposure to the provocative agent methacholine, eosinophil infiltration of the airways, goblet cell hyperplasia and serum IgE secretion, as compared to control BALB/c mice challenged with PBS (FIG. 1).

By contrast administration of anti-IL-25 mAb prior to each sensitization and aerosolization with OVA resulted in a marked abrogation in AHR following challenge with aerosolised methacholine, with resistance values comparable to the PBS control mice (FIG. 1A). Administration of an isotype-matched control mAb did not suppress AHR (FIG. 1A).

The anti-IL-25 mAb also significantly reduced the levels of cellular infiltration around the lung vasculature (FIGS. 1B and 3A), goblet cell hyperplasia in the airways (FIGS. 1C and 3B) and levels of antigen-specific serum IgE (FIG. 1D).

Analysis of bronchoalveolar lavage (BAL) demonstrated that eosinophil infiltration was also significantly suppressed following anti-IL-25 mAb administration as compared to the isotype-control treated mice (FIG. 1E). Since type-2 cytokines are known to regulate these effector functions we determined the levels of cytokines secreted from cells isolated from the draining mediastinal lymph nodes following antigen restimulation. In contrast to the elevated levels of type-2 cytokines, IL-4, IL-5 and IL-13, induced by OVA sensitization and challenge in BALB/c mice, administration of anti-IL-25 mAb resulted in a significant reduction in the levels of these cytokines (FIG. 1F).

These data support the hypothesis that by blocking IL-25 signalling we have constrained the production of type-2 cytokines leading to the abrogation of the type-2 effector functions, including inflammation and AHR. Thus, antagonists of IL-25 effectively suppress type-2 inflammation if administered from the initiation of the response.

Materials and Methods:

Mice

BALB/c mice were obtained from Harlan UK and maintained in the SABU/CBS or National Heart and Lung Institute facilities in specific pathogen free environments. All animal experiments outlined in this report were undertaken with the approval of the UK Home Office.

Sensitization and Allergen Exposure

BALB/c mice (6-12 weeks) were sensitised by intraperitoneal administration of ovalbumin (20 µg/injection) complexed with alum, or alum only (controls), at days 0 and 12. Aerosol administration of 1% ovalbumin was undertaken on days 19, 20, 21 for 20 minutes per day. On day 22 the animals were analysed using plethysmography to assess AHR.

Administration of Anti-rmIL-25 Monoclonal Antibodies

Airways hyperresponsiveness (AHR) was induced as described and anti-IL-25 mAb (500 µg/dose) was administered intraperitoneally the day before each intraperitoneal OVA sensitisation, the day before the initial OVA challenge into the lungs and 4 hours prior to each OVA aerosolisation. In further experiments anti-IL-25 mAb (500 µg/dose) was administered intraperitoneally only on the day but before each aerosolisation. Control mice received either saline or isotype control (500 µg/dose) instead of anti-IL25 mAb. Isotype control was anti-c-myc (mouse IgG1, clone 9E10.2).

Measurement of Airway Responsiveness

Animals were anaesthetized, tracheostomised and placed on a ventilator (SAR-830 series, CWE Inc) at a rate of 150 breaths/min, with a tidal volume of 0.2 ml. Mice were monitored in a whole body plethysmograph (EMKA Technologies, Paris) and transpulmonary pressure was assessed via an inline transducer. After recording stable baseline pulmonary resistance, increasing concentrations of acetyl-β-methylcholine chloride (methacholine) (Sigma, Dorset, UK) were administered by aerosol for 15 s at each concentration with an ultrasonic nebulizer, and pulmonary resistance was recorded for a 5 min period. IOX software was used to analyse airways resistance, compliance and standard pulmonary parameters.

Bronchoalveolar Lavage (BAL)

Mice were killed by cervical dislocation and 4×500 µl aliquots of PBS were injected through the tracheostomy and retrieved. Differential cell counts on 150 cells were performed on cytospins stained with giemsa.

Example 3

Administration Prior to Challenge

Figure 2:
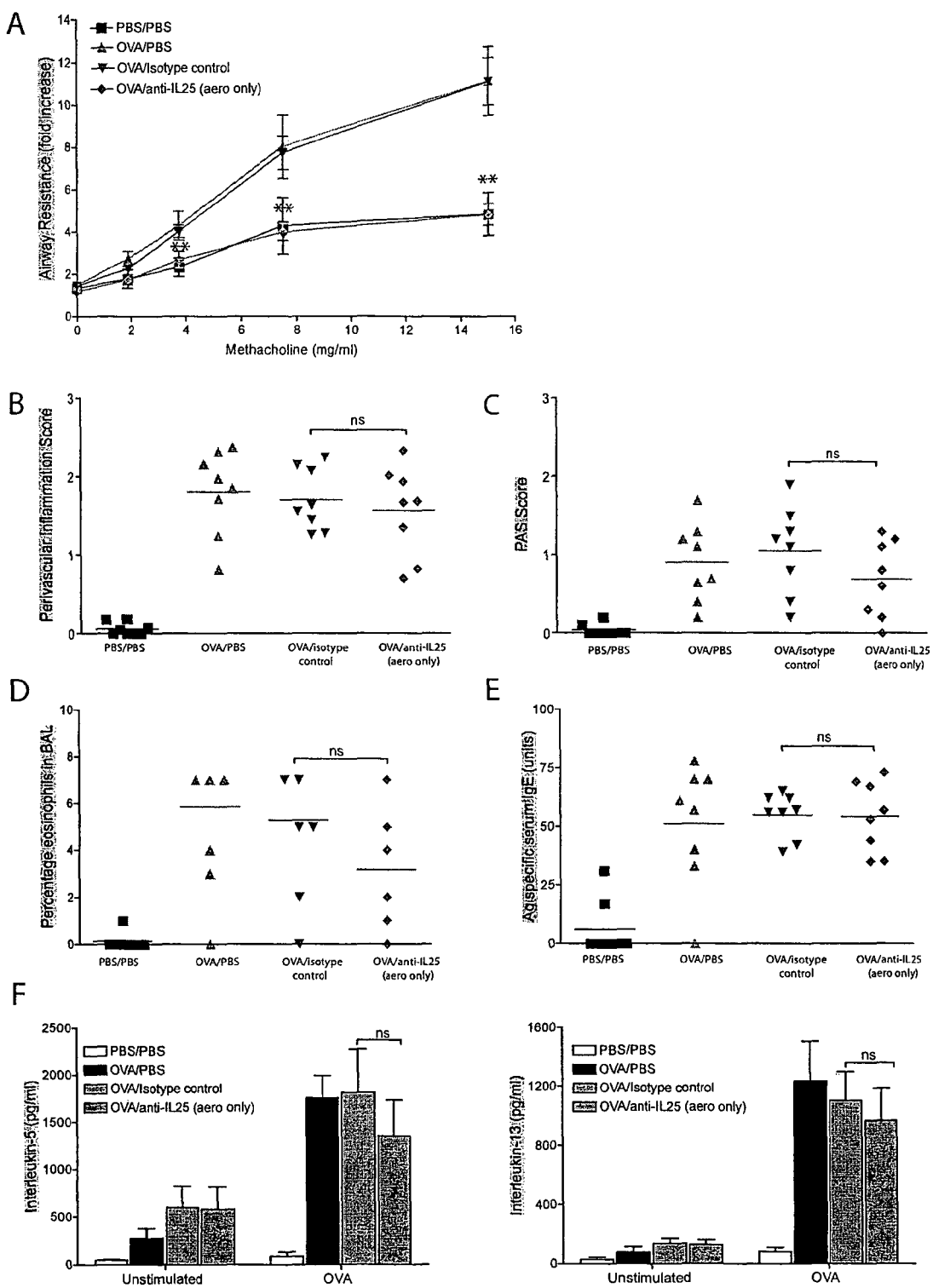
FIG. 2 shows neutralisation of IL-25 during asthma challenge only. (A) Methacholine sensitivity of OVA-sensitised mice was determined one day after the last aerosolised antigen challenge. Data are combined from 2 experiments and represent the mean±SEM of 14-18 mice/group. (*$p<0.05$ versus isotype control, **$p<0.01$ versus isotype control) (B) Lung sections were stained with giemsa and scored for perivascular infiltration, n=8 per group. (C) Mucus content was determined by periodic acid Schiff (PAS) staining of lung sections, n=8 per group. (D) The proportion of eosinophils in BAL was determined by differential cell counting of cytospins stained with giemsa, n=6 per group. (E) Antigen-specific serum IgE was measured by ELISA, OD reading were converted to arbitrary units by comparison with a standard serum n=8 per group. (F) Antigen-induced cytokine production from restimulated mediastinal lymph node cells. Protein levels were determined by ELISA, n=6 per group. Symbols represent individual animals and the mean is represented by a bar. Data are representative of at least 2 independent experiments. Sens=antibody administered prior to sensitization, aero=antibody administered 4 hours prior to each aerosol challenge.

We also assessed whether the anti-IL-25 mAb was effective when administered only prior to the OVA aerosolisation challenge. Treatment with the anti-IL-25 mAb dramatically reduced the airways resistance induced by methacholine provocation even when it was given later in the response (FIG. 2A). By contrast, administration of the control isotype-matched mAb did not abrogate AHR.

Significantly, analysis of lung histology sections showed no significant changes in the levels of cellular infiltrate around blood vessels (FIG. 2B) or airway goblet cell hyperplasia (FIG. 2C) between anti-IL-25 mAb treated mice and the OVA challenged BALB/c controls or the isotype-matched mAb treated controls.

Furthermore, there was no observable reduction in the proportion of eosinophils in the BAL fluid (FIG. 2D) or the levels of antigen-specific serum IgE (FIG. 2E), following anti-IL-25 mAb administration. Strikingly, the levels of the type-2 cytokines IL-5 and IL-13 remained comparable to those of the OVA challenged BALB/c controls or the isotype-matched mAb treated controls following antigen restimulation (FIG. 2F), and IL-13 levels in the BAL were also unchanged. Thus, anti-IL-25 administration during the challenge phase of the response can specifically abrogate AHR even when the type-2 cytokines and their downstream effectors are not down-regulated. These findings suggest that IL-25 may initiate AHR by a pathway that is independent of the classical type-2 response.

Materials and Methods

Materials and methods were as described above for example 2, with the addition of:

Lung Tissue Collection and Histology

Lungs were fixed in Formalin (10% formaldehyde in 0.9% saline solution) for histological analysis. Lung sections were stained with giemsa for inflammatory infiltrate and periodic acid-Schiff (PAS) for goblet cells. PAS-stained goblet cells in airway epithelium were measured blind using a numerical scoring system (0: <5% goblet cells; 1: 5-25%; 2: 25-50%; 3: 50-75%; 4: >75%). The sum of airway scores from each lung was divided by the number of airways examined, 20-40 airways/mouse, and expressed as PAS score in arbitrary units. Inflammation was evaluated using a numerical scoring system to assess numbers of infiltrating cells around blood vessels (0: layer of infiltrating inflammatory cells <2 cells thick around vessel, 1: 2-4 cells thick, 2: 5-8 cells thick, 3>8 cells thick). The sum of airway scores from each lung was divided by the number of vessels examined, 20-40 airways/mouse, and expressed in arbitrary units.

Example 4

IL-25 Acts Via a Type-2-Independent Pathway

Figure 3:
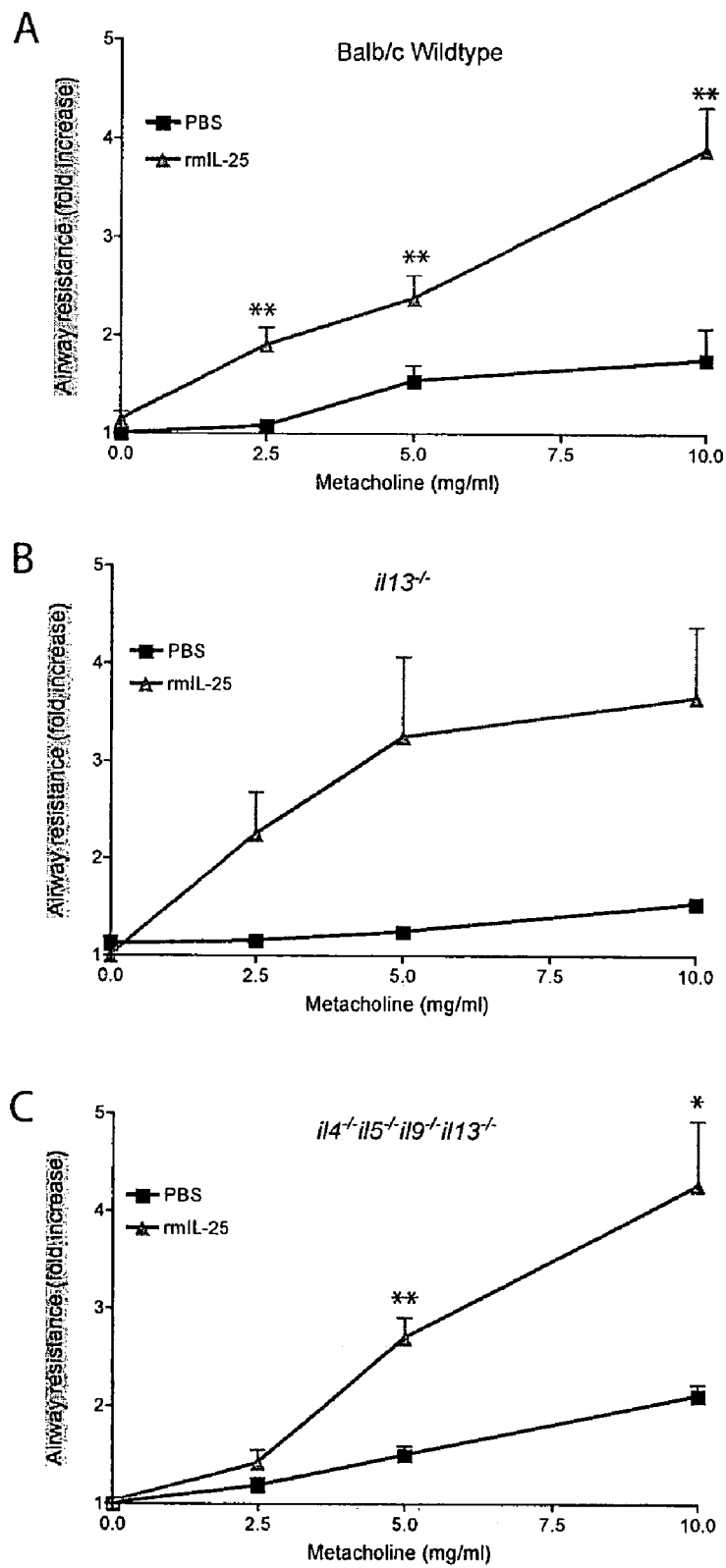
FIG. 3 shows administration of rmIL-25 to naïve mice. Wildtype (A), il13$^{-/-}$ (B) or il4$^{-/-}$ il5$^{-/-}$ il9$^{-/-}$ il13$^{-/-}$ (C) mice were administered 1.8 µg rIL-25 or PBS intranasally. Methacholine sensitivity was determined 16 hours after challenge. *$p<0.05$ versus isotype control, **$p<0.01$ versus isotype control, n=4-8 per group. Data are representative of at least 2 independent experiments.

We assessed whether exogenously administered rmIL-25 could elicit enhanced AHR even in the absence of antigen sensitisation or challenge. As early as 16 hours post intranasal administration of rmIL-25 to BALB/c mice we detected significantly elevated airways resistance (FIG. 3A). Previous reports have indicated the central role played by IL-13 in the asthma phenotype and particularly AHR. To determine if IL-25 was mediating its role in AHR through IL-13 we administered rmIL-25 to il13$^{-/-}$ mice. Once again we observed elevated AHR following rmIL-25 treatment (FIG. 3B). Since the other type-2 cytokines have also been shown to contribute to the asthma phenotype we also assessed the response of il4$^{-/-}$ il5$^{-/-}$ il9$^{-/-}$ il13$^{-/-}$ to rmIL-25 administered intranasally. Even in the absence of all of the classical type-2 cytokines IL-25 treatment enhanced AHR following methacholine provocation (FIG. 3C). These data support a role for IL-25 in exacerbating AHR through a type-2 cytokine-independent pathway.

Materials and Methods

Materials and methods were as described above for examples 2 and 3, with the addition of:

Mice

Transgenic il4$^{-/-}$ il5$^{-/-}$ il9$^{-/-}$ il13$^{-/-}$ mice (P. G. Fallon et al., 2002. *Immunity* 17, 7) and il13$^{-/-}$ mice (G. J. McKenzie et al., 1998. *Curr Biol.* 8, 339) on a BALB/c background were as described. Il25$^{-/-}$ mice on a C57BL/6×129 F2 background were as described (P. G. Fallon et al. 2006. *J. Exp. Med.* 203, 1105).

Intranasal IL-25 Administration

Mice were administered with 1.8 µg of rIL-25 (R&D Systems) or 1.8 µg of rIL-13 (Peprotech) in 40 µl PBS per mouse intranasally on day 0. Control animals received PBS only.

Example 5

Cloning 2C3 Variable Domains

RNA from three sub clones of 2c3 was isolated and cDNA prepared by a reverse transcription reaction.

The immunoglobulin heavy chain (IgH) cDNA was amplified by PCR using a conserved 5' VH region primer, MHV7 (SEQ ID NO:11) in combination an IgG1 constant region primer MHCG1 (SEQ ID NO:12).

Similarly, immunoglobulin light chain (IgK) was amplified using a conserved 5' IgK region primers MKV9 (SEQ ID NO:13) in combination with the kappa constant region primer MKC (SEQ ID NO:14).

The thermostable polymerase Phusion (NEB F-531L) was used throughout for PCR reactions.

The 2c3 amplification products of VH7+MHCG1-primed the PCR reactions from three independent cDNAs, were directly ligated into the pCRII®Blunt-TOPO® vector using the TOPO-blunt cloning® kit (Cat 45-0245), as were the amplification products of the light chain amplification reaction. E. coli TOP10 bacteria transformed with the ligated pCRII-blunt vector constructs were cloned on LB-ampicillin-XGal agar plates, by picking white colonies onto an agar grid and into the PCR screening mixture. The cloned plasmid inserts were PCR-amplified. The amplification products were gel electrophoresed and the predicted products identified. Overnight cultures (5 ml) of each clone, producing the correct-sized PCR amplification product, were processed using the QIAprep Spin Miniprep Kit Protocol (cat 27106), to produce DNA plasmid minipreps.

Plasmids were sequenced using the BigDye® Terminator v3.0 Cycle Sequencing Ready Reaction Kit (ABI cat. 4390242). Each selected plasmid was sequenced in both directions using M13 forward and reverse primers cycled on a GeneAmp9600 PCR machine. The electrophoretic sequence analysis was done on an ABI capillary sequencer.

The complete cycle of RT-PCR, cloning, and DNA sequence analysis was repeated to obtain three completely independent sets of sequence information for each immunoglobulin chain.

The complete deduced nucleotide sequence of the VH and Vkappa genes are shown as SEQ ID NO:15 and SEQ ID NO:16 respectively. These sequences include the leader sequences at the beginning of each variable gene segment which encodes a signal sequence which is used to transport the newly synthesized antibody chains into the endoplasmic reticulum; they is not present in the final heavy and light chains.

REFERENCES

1. P. G. Fallon et al., *Immunity* 17, 7 (July, 2002).
2. G. Grunig et al., *Science* 282, 2261 (1998).
3. M. Wills-Karp et al., *Science* 282, 2258 (1998).
4. M. M. Fort et al., *Immunity* 15, 985 (December, 2001).
5. M. R. Kim et al., *Blood* 100, 2330 (Oct. 1, 2002).
6. G. Pan et al., *J Immunol* 167, 6559 (Dec. 1, 2001).
7. S. D. Hurst et al., *J Immunol* 169, 443 (Jul. 1, 2002).
8. T. A. Moseley, D. R. Haudenschild, L. Rose, A. H. Reddi, *Cytokine Growth Factor Rev* 14, 155 (April, 2003).
9. P. G. Fallon et al., *J Exp Med* 203, 1105 (Apr. 17, 2006).
10. A. M. Owyang et al., *J Exp Med* 203, 843 (Apr. 17, 2006).
11. T. Tamachi et al., *J Allergy Clin Immunol* 118, 606 (September, 2006).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The invention claimed is:

1. A target binding member that binds interleukin 25 (IL-25) and which comprises an antibody VH domain comprising a VH CDR1 having an amino acid sequence that is identical to SEQ ID NO:5, a VH CDR2 having an amino acid sequence that is identical to SEQ ID NO:6 and a VH CDR3 having an amino acid sequence that is identical to SEQ ID NO:7, and which further comprises an antibody VL domain comprising a VL CDR1 having an amino acid sequence that is identical to SEQ ID NO:8, a VL CDR2 having an amino acid sequence that is identical to SEQ ID NO:9 and a VL CDR3 having an amino acid sequence that is identical to SEQ ID NO:10.

2. A target binding member that binds interleukin 25 (IL-25) and which comprises an antibody VH domain comprising SEQ ID NO:2.

3. The target binding member of claim 2 which further comprises a VL domain with a CDR1 having an amino acid sequence that is identical to SEQ ID NO:8, a CDR2 having an amino acid sequence that is identical to SEQ ID NO:9 and a CDR3 having an amino acid sequence that is identical to SEQ ID NO:10.

4. The target binding member of claim 3 wherein the VL domain comprises a human framework region.

5. A target binding member that binds interleukin 25 (IL-25) and which comprises an antibody VH domain comprising SEQ ID NO:2 and an antibody VL domain comprising SEQ ID NO:4.

6. The target binding member of claim 2 which is a Fab, F(ab')$_2$, or scFv antibody fragment.

7. The target binding member of claim 2 which comprises an antibody constant region.

8. The target binding member of claim 7 wherein the constant region is an IgG1 or IgG4 constant region.

9. The target binding member of claim 7 which comprises a whole antibody.

10. An isolated nucleic acid which comprises a nucleotide sequence encoding the target binding member of claim 2.

11. An expression vector comprising the nucleic acid of claim 10 operably linked to a promoter.

12. A host cell transformed with the expression vector of claim 11.

13. A method of producing a target binding member, the method comprising culturing host cells according to claim 12 under conditions for production of said target binding member.

14. The method according to claim 13 further comprising isolating said target binding member.

15. The method according to claim 13 further comprising formulating the target binding member into a composition including at least one additional component.

16. A composition comprising the target binding member of claim 2 and a pharmaceutically acceptable carrier.

17. The composition of claim 16 in the form of a lyophilized powder.

18. A method for the treatment or prevention of asthma, said method comprising administering to a subject in need of treatment an effective amount of the target binding member of claim 2.

* * * * *